United States Patent
Hernandez-Garcia et al.

(10) Patent No.: US 10,136,824 B2
(45) Date of Patent: Nov. 27, 2018

(54) ARTERIAL SPIN LABELING (ASL) WITH MAGNETIC RESONANCE FINGERPRINTING (MRF)

(71) Applicant: Case Western Reserve University, Cleveland, OH (US)

(72) Inventors: Luis Hernandez-Garcia, Ann Arbor, MI (US); Mark Griswold, Shaker Heights, OH (US); Dan Ma, Cleveland Heights, OH (US); Vikas Gulani, Cleveland Heights, OH (US); Katherine L. Wright, Macedonia, OH (US); Yun Jiang, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 880 days.

(21) Appl. No.: 14/690,524

(22) Filed: Apr. 20, 2015

(65) Prior Publication Data

US 2015/0297101 A1 Oct. 22, 2015

Related U.S. Application Data

(60) Provisional application No. 61/982,588, filed on Apr. 22, 2014.

(51) Int. Cl.
*A61B 5/026* (2006.01)
*A61B 5/055* (2006.01)
(Continued)

(52) U.S. Cl.
CPC .......... *A61B 5/0263* (2013.01); *A61B 5/055* (2013.01); *A61B 5/4064* (2013.01);
(Continued)

(58) Field of Classification Search
CPC .......... G01R 33/56563; G01R 33/5602; G01R 33/5608; G01R 33/5611; G01R 33/448;
(Continued)

(56) References Cited

U.S. PATENT DOCUMENTS

| | | | | |
|---|---|---|---|---|
| 2015/0301138 A1* | 10/2015 | Griswold | ......... | G01R 33/56563 324/309 |
| 2015/0301144 A1* | 10/2015 | Griswold | ......... | G01R 33/56563 324/309 |
| 2015/0301147 A1* | 10/2015 | Gulani | ............ | G01R 33/56563 324/309 |

OTHER PUBLICATIONS

Wright et al., Theoretical Framework for MR Fingerprinting with ASL: Simultaneous Quantification of CBF, Transit Time, and T1, Proc. Intl. Soc. Mag. Reson. Med. 22, 2014.*

(Continued)

*Primary Examiner* — Bo J Peng
(74) *Attorney, Agent, or Firm* — Quarles & Brady LLP

(57) ABSTRACT

Example apparatus and methods perform magnetic resonance fingerprinting (MRF) for arterial spin labeling (ASL) based parameter quantification. ASL with MRF produces a nuclear magnetic resonance signal time course from which simultaneous quantification of ASL perfusion-related parameters can be achieved. The parameters may include cerebral blood flow, transit time, T1, or other parameters. The quantification uses values from a dictionary of signal time courses that were generated or augmented using Bloch simulation, knowledge of the sequence, or previous observations. The dictionary may account for inflow or outflow of labeled spins and may model arterial input. An ASL-MRF pulse sequence may differ from conventional pulse sequences. For example, an ASL-MRF pulse sequence may include non-uniform control pulses, non-uniform label pulses, non-uniform post labeling delay time, non-uniform (Continued)

background suppression pulses, non-uniform acquisition repetition time, or non-uniform acquisition flip angle.

27 Claims, 9 Drawing Sheets

(51) Int. Cl.
*G01R 33/44* (2006.01)
*G01R 33/48* (2006.01)
*G01R 33/565* (2006.01)
*G01R 33/56* (2006.01)
*G01R 33/561* (2006.01)
*G01R 33/563* (2006.01)
*A61B 5/00* (2006.01)
*A61B 1/00* (2006.01)
*G01R 1/00* (2006.01)
*G01R 33/50* (2006.01)

(52) U.S. Cl.
CPC ....... *G01R 33/448* (2013.01); *G01R 33/4818* (2013.01); *G01R 33/5602* (2013.01); *G01R 33/5608* (2013.01); *G01R 33/5611* (2013.01); *G01R 33/56366* (2013.01); *G01R 33/56563* (2013.01); *A61B 1/00* (2013.01); *A61B 5/742* (2013.01); *A61B 2217/00* (2013.01); *A61B 2218/00* (2013.01); *G01R 1/00* (2013.01); *G01R 33/4828* (2013.01); *G01R 33/50* (2013.01)

(58) Field of Classification Search
CPC .......... G01R 33/56366; G01R 33/4828; G01R 33/50; G01R 33/4818; A61B 5/4064; A61B 5/0263; A61B 5/055; A61B 5/742
See application file for complete search history.

(56) References Cited

OTHER PUBLICATIONS

Wright et al., Estimation of perfusion properties with MR Fingerprinting Arterial Spin Labeling, Magnetic Resonance Imaging 50, 2018, 68-77.*

Ma et al., Magnetic resonance fingerprinting, Nature, vol. 495, Mar. 14, 2013, 187-193.*

* cited by examiner

ARTERIAL SPIN LABELING (ASL) WITH MAGNETIC RESONANCE FINGERPRINTING (MRF)

CROSS REFERENCE TO RELATED APPLICATIONS

This application claims the benefit of U.S. Provisional Patent Application 61/982,588 filed Apr. 22, 2014.

STATEMENT REGARDING FEDERALLY SPONSORED RESEARCH

This invention was made with government support under grant EB017219 awarded by National Institutes of Health. The government has certain rights in the invention.

BACKGROUND

Blood moves around in the body in the veins and arteries. Blood carries oxygen from place to place and also carries carbon dioxide from place to place. Perfusion is the process of blood being delivered to a capillary bed in a biological tissue. Blood includes water. Since water is made from hydrogen and oxygen, water is particularly susceptible to being excited by magnetic resonance imaging (MRI) apparatus where radio frequency (RF) energy applied at a specific frequency and in specific orders in a controlled magnetic field produce nuclear magnetic resonance (NMR) in resonant species (e.g., hydrogen). The NMR may occur in the hydrogen atoms, which may be referred to as "spins." These attributes of blood led to the development of arterial spin labelling (ASL).

In ASL, water in arterial blood is magnetically labeled and then the effect produced by transiting or transited arterial blood is imaged. Since the blood moves around the body, the blood may be magnetically labeled in a first place and then produce an effect that is imaged in a different place. For example, arterial blood water may be magnetically labeled outside a region of interest (RoI). The blood may then move into the RoI where it may, for example, exchange with tissue water. The inflowing labeled spins may change the total tissue magnetization in the RoI or in a portion of the RoI. This change in magnetization may be detectable by MRI. The time between when the spins are labelled and the time when an image is taken is called the transit time because it is the time during which the labeled spins transit from place to place. The time during which the spins are labeled is called the tag time because it is the time during which the spins are "tagged" for use in imaging.

Conventional MRI produces images that may vary between scanners, technologists, or scan settings. Conventional MRI images are interpreted qualitatively, which produces subjective variability in diagnosis. Unlike conventional MRI, magnetic resonance fingerprinting (MRF) provides consistent quantitative parameters maps, which eliminates the variability found in conventional qualitative images. Quantitative parameter maps also reduce or eliminate subjectivity in diagnosis. In MRF, unique signal time courses are generated for pixels. The time courses evolve based on the properties of the material subjected to MRF including T1 and T2, T1 being spin-lattice relaxation, and T2 being spin-spin relaxation.

The signal time course can be matched to an entry in a dictionary. The dictionary may be, for example, a collection of time courses calculated using a range of possible property values in light of quantum physics properties that govern the signal evolution. Performing MRF for multiple pixels yields maps of material properties of interest. MRF may be more efficient than other proposed quantitative methods. In addition, MRF quantifies multiple parameters in a single MR acquisition.

MRF assumes that different materials and different spatial locations have different signal evolutions. In MRF, different materials may be separated by varying user-controllable MR settings including flip angle (FA) and acquisition periods in, for example, a pseudo-random fashion. Randomized encoding may be used to separate different spatial locations.

MRF employs a series of varied sequence blocks that simultaneously produce different signal evolutions in different resonant species (e.g., tissues) to which radio frequency (RF) energy is applied. MRF sequence blocks may vary widely, either non-linearly, randomly, and/or pseudo-randomly. Since the sequence blocks may vary widely, the resulting signal evolutions may also vary widely.

The term "resonant species", as used herein, refers to an item (e.g., water, fat, tissue, material, blood, arterial blood water, hydrogen in arterial blood water) that can be made to resonate using NMR. By way of illustration, when RF energy is applied to a volume that has bone and muscle tissue, then both the bone and muscle tissue will produce an NMR signal. However the "bone signal" and the "muscle signal" will be different and can be distinguished using MRF. The different signals can be collected over a period of time to identify a signal evolution for the volume. Resonant species in the volume can then be characterized by comparing the signal evolution to known evolutions. Characterizing the resonant species may include identifying a material or tissue type, or may include identifying MR parameters associated with the resonant species. The "known" evolutions may be, for example, simulated evolutions or previously acquired evolutions. A large set of known evolutions may be stored in a dictionary.

Characterizing the resonant species can include identifying different properties of a resonant species (e.g., T1, T2, diffusion resonant frequency, diffusion co-efficient, spin density, proton density). Additionally, other properties including, but not limited to, tissue types, materials, and super-position of attributes can be identified. These properties may be identified simultaneously using MRF, which is described in U.S. Pat. No. 8,723,518 "Nuclear Magnetic Resonance (NMR) Fingerprinting" and in *Magnetic Resonance Fingerprinting*, Ma et al., Nature 495, 187-192 (14 Mar. 2013), the contents of both of which are incorporated herein by reference.

DETAILED DESCRIPTION

Figure 1:
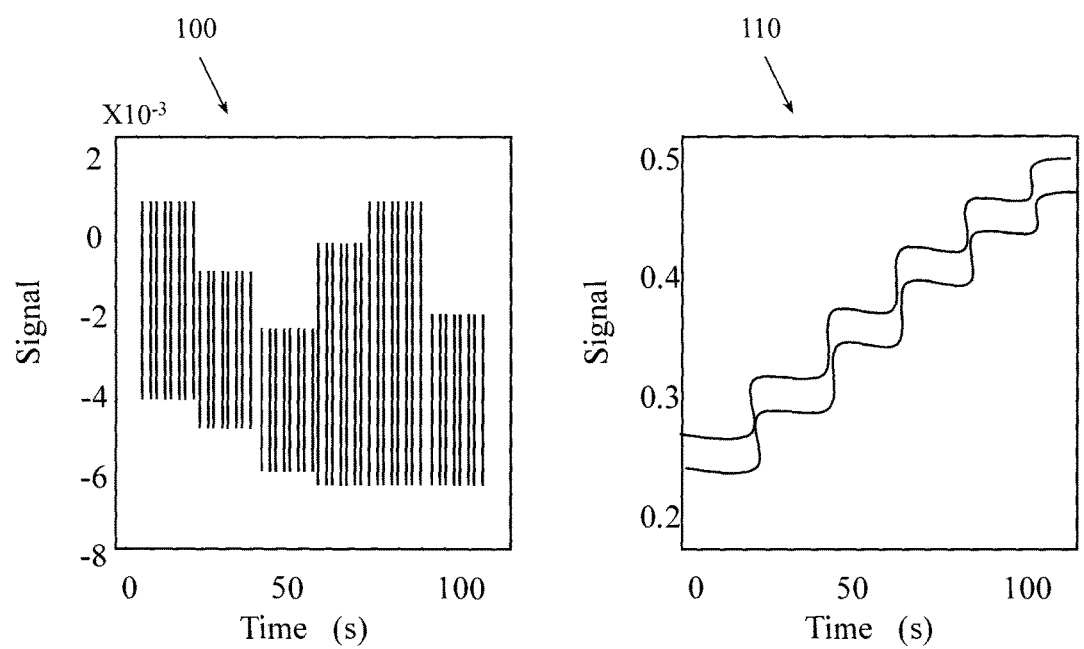
FIG. 1 illustrates simulated signal changes due to transit time and perfusion effects.

Example apparatus and methods perform magnetic resonance fingerprinting (MRF) for arterial spin labeling (ASL) based parameter quantification. MRF has been demonstrated as an accurate and efficient approach for simultaneous quantification of multiple physical or physiological parameters. Example apparatus and methods may perform ASL with MRF and then perform simultaneous quantification of ASL perfusion-related parameters including cerebral blood flow (CBF), transit time, T1, or other parameters.

Conventional ASL methods may require unacceptably long acquisition times. Additionally, conventional perfusion quantitation may require knowledge of several tissue properties. Example apparatus and methods may perform MRF to quantify ASL perfusion-related parameters with shorter acquisition times than conventional approaches and with less a priori knowledge of tissue properties required than for conventional approaches.

In MRF, a unique signal time course is generated for a pixel. The time course is based on properties of materials of interest (e.g., hydrogen in arterial blood water). A dictionary of signal time courses may be generated or augmented using Bloch simulation and knowledge of the sequence. A dictionary may also be generated or augmented with previous observations. Template matching or other comparison techniques may be applied to an acquired signal time course to identify a match or related signal time course in the dictionary. The dictionary entry can be used as, for example, an index to retrieve underlying parameters associated with the dictionary entry.

For ASL-MRF, signal time courses that are associated with different perfusion-related parameters (e.g., CBF, transit time, tissue T1) may be employed. In one embodiment, the signal time courses may be generated by modifying a pulse sequence with a pseudo-continuous (PCASL) labelling scheme so that labeled spins are delivered to a target tissue over time according to a variable arterial input function. A dictionary of signal evolutions that accounts for inflow and outflow of labeled spins may be created using:

$$\frac{dM}{dt} = \frac{M_0 - M}{T_1} + fM_a(t) - \frac{f}{\lambda}M \qquad [1]$$

and by modeling the arterial input using:

$$M_a(t) = M_0(1 - 2\alpha e^{-\Delta t/T_{1,a}}) * k(t - \Delta t), \text{ if } L(t) = 1 \qquad [2]$$

$$M_a(t) = M_0(1 - e^{-\Delta t/T_{1,a}}) * k(t - \Delta t), \text{ if } L(t) \neq 1 \qquad [3]$$

where M is the magnetization in brain tissue, $M_0$ is the default or equilibrium tissue magnetization, $T_1$ and $T_{1,a}$ are the $T_1$ values for tissue and blood, $M_a(t)$ is the magnetization of labeled arterial blood, f is perfusion, $\lambda$ is a blood volume fraction associated with how much of a voxel is filled with blood, a is an inversion imperfection factor that accounts for the fact that the inversion may not be perfect is, $\Delta t$ is the transit time of blood, $k(t-\Delta t)$ is a function (e.g., Gamma-variate function) to capture arterial dispersion, and L(t) is the labeling function that indicates the occurrence of inversion pulses (L(t)=1).

Using a dictionary built at least in part using signal evolutions that are a function of the equations 1-3, a pattern recognition function (e.g., maximum inner product, minimization of error) may identify dictionary entries that are related to (e.g., match, best match) an acquired signal. The matching entry or entries may then be used to retrieve parameters including but not limited to CBF, transit time, and $T_1$.

In one embodiment, acquisition periods and tagging duration may be varied. For example, the labeling function L(t) may be varied through an acquisition. In one experiment performed to validate example apparatus and methods, L(t)=1 was used during labeling pulses, L(t)=−1 was used during control pulses, and L(t)=0 was used during post label decay and data acquisition. More generally, L(t) may be positive during labeling pulses, negative during control pulses, and zero during post label decay and data acquisition. Other values and schemes for L(t) may be employed. Labeling duration and acquisition periods may be linearly increased with alternating labeling/control pulses. Other schemes for varying parameters may be employed. For example, a sequence may include a pseudo-randomly or uniquely varied occurring labeling/control pulses. In another embodiment, a sequence may be altered to contain inversion or saturation pulses to generate MRF ASL signals. In different embodiments, sequence parameters (e.g., post labeling delay time, occurrence of background suppression pulses, acquisition period, acquisition flip angle) may be randomized.

To verify the performance of example apparatus and methods, experiments were performed to evaluate the ability of MRF ASL to select an appropriate dictionary entry at different signal to noise ratio (SNR) levels. An example dictionary was created by varying the T1 of tissue (0.4-1.6 s, 0.05 s step size), f(0.001-0.02 ml/s/g, 0.001 ml/s/g step size), and Δt (0.5-2.5 s, 0.05 s step size), yielding a total of 20,5000 entries. An ideal signal curve representing a time series of images was created by selecting a single entry in the simulated dictionary and random noise was added to the curve for ten different SNR values. SNR was computed by taking the maximum signal from the ideal curve and the standard deviation of the added noise.

FIG. 1 illustrates signal changes due to transit time and perfusion effects and T1 of material. Image 100 relates signal to time for a flow dependent example. For image 100, f=0.01, 0.02 ml/s/g and Δt=1,1.2 s. Image 110 relates signal to time for a flow independent example. For image 110, T1=1.2 s, 1.4 s. Images 100 and 110 verify the performance of example apparatus and methods.

Figure 2:
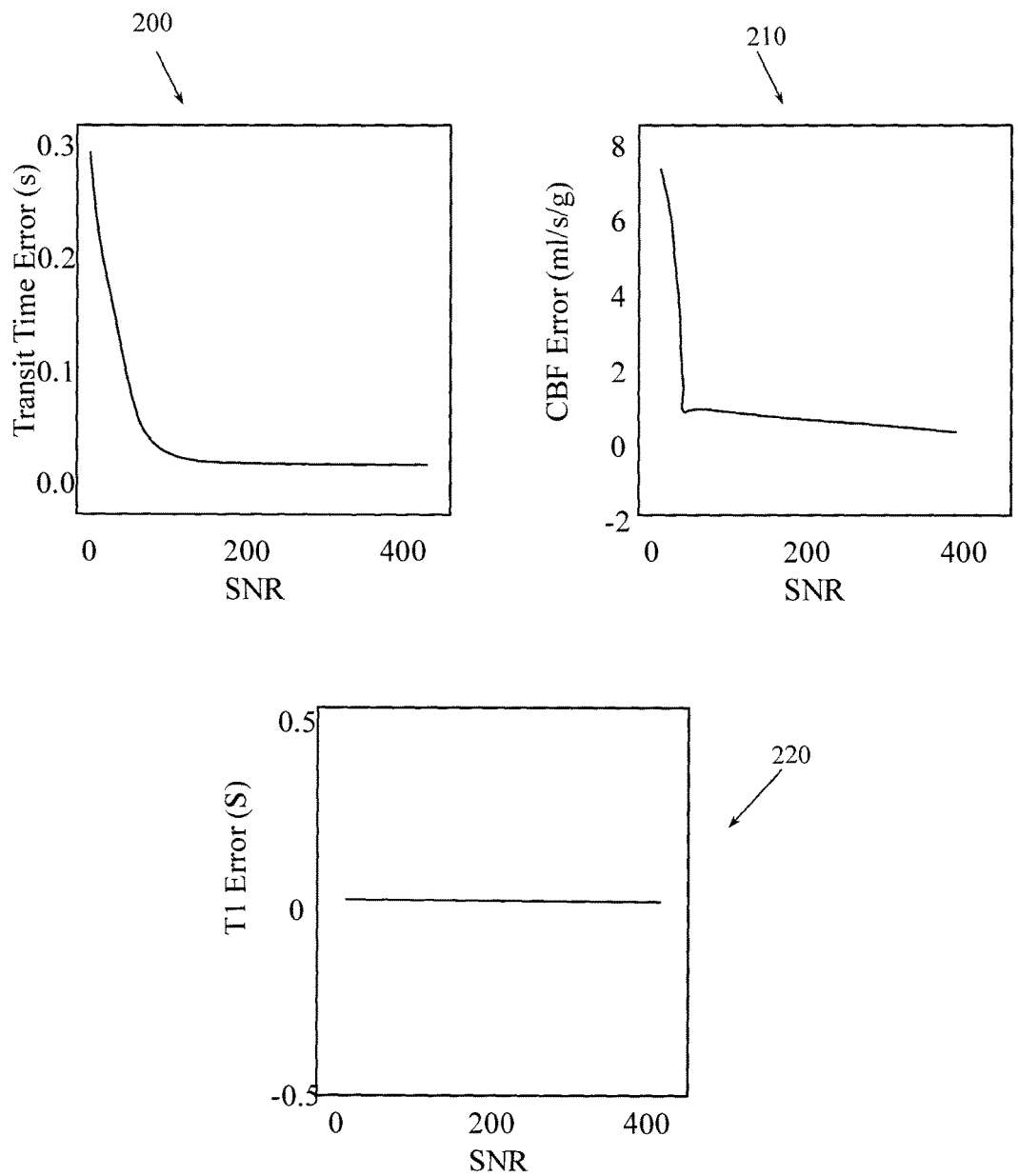
FIG. 2 illustrates quantitative accuracy at different signal to noise (SNR) levels.

FIG. 2 illustrates results of parameter accuracy estimations at different SNR levels for a time series of images. Image 200 compares SNR to transit time error (measured in seconds). Image 210 compares SNR to CBF error (measured in ml/s/g). Image 220 compares SNR to T1 error (measured in seconds). Signal changes in the time course related to T1 relaxation are large, which results in accurate T1 estimation at all SNR levels tested. Signal changes in the time course related to CBF and transit time are small, which results in increased error at lower SNR values. Because signal changes for transit time and CBF are smaller, they are more sensitive to noise than T1.

Figure 3:
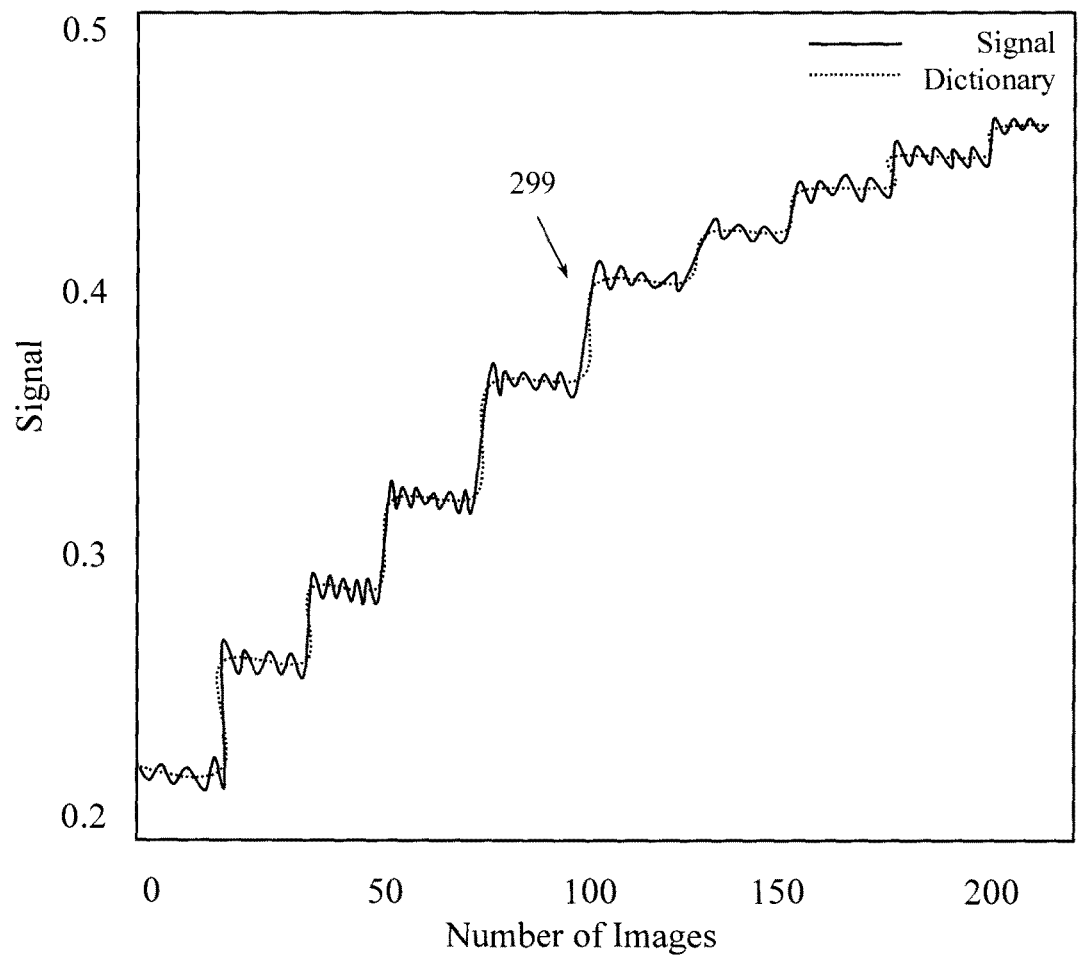
FIG. 3 illustrates signal generated with an SNR value of 98 and the best fit.

FIG. 3 illustrates a curve 299 with an SNR of 98 and a matched dictionary entry. Curve 299 illustrates a good match between the noisy signal and dictionary entry. The errors in perfusion and transit time were 0.001 ml/s/g and 0.05 s, respectively.

The results illustrated in FIGS. 1-3 demonstrate that MRF may be used to accurately estimate perfusion parameters for ASL. The many degrees of freedom available in MRF sequence design facilitate generating signal time courses in different ways than was possible for conventional ASL. For example, label/control pulses do not need to occur in pairs, which alleviates an issue with conventional approaches. The number, location, or order of control/label pulses may be randomly selected. Additionally or alternatively, the duration of control/label pulses may be randomly selected. Other sequence parameters may also be randomized. With the additional flexibility in sequence design available in MRF ASL, efficiency and accuracy for ASL perfusion quantification are improved over conventional systems.

Figure 4:
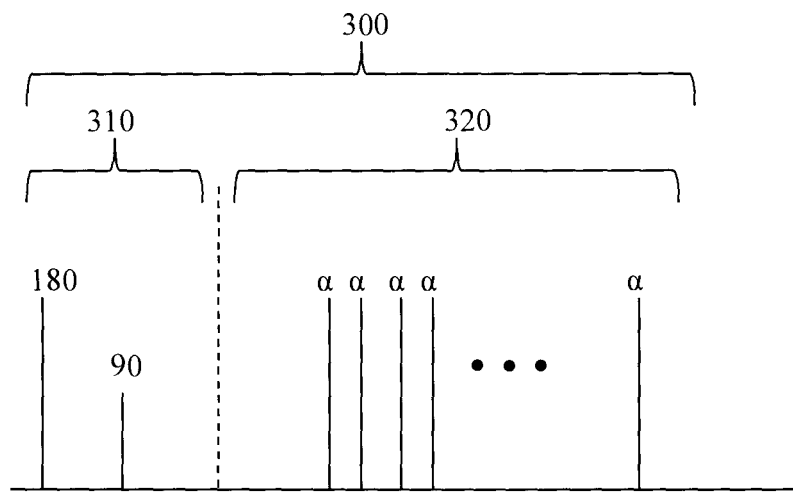
FIG. 4 illustrates an example MRF pulse sequence.
Figure 4:
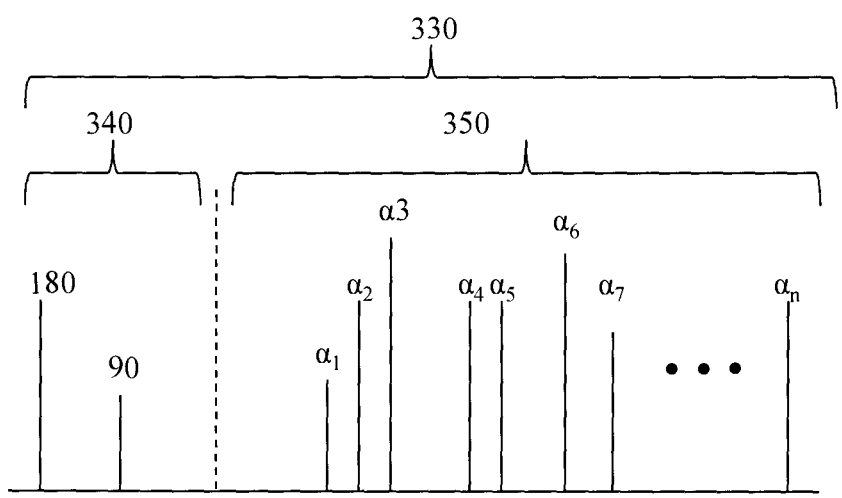

Magnetic resonance (MR) uses pulse sequences. In MRF, the pulse sequences may vary from sequence block to sequence block. FIG. 4 compares and contrasts conventional sequence blocks to example sequence blocks. Sequence block 300 includes a preparation phase 310 and an acquisition phase 320. During acquisition phase 320, multiple acquisitions using the same flip angle and the same interval between acquisitions may be performed. Acquisition phase 320 resembles a prior approach that acquires data from a (k, t) space, where t varies either constantly or linearly. The constant variation facilitates acquiring signal with constant amplitude and phase as required for conventional image reconstruction.

Sequence block 330 also includes a phase 340 and an acquisition phase 350. Notice that acquisition phase 350 is much longer than acquisition phase 320. Unlike acquisition phase 320 where parameters are either fixed or vary linearly, in acquisition phase 350 the parameters may vary widely, either non-linearly, randomly, and/or pseudo-randomly. Sequence blocks may vary in a number of parameters including, but not limited to, echo time, flip angle, phase encoding, diffusion encoding, flow encoding, RF pulse amplitude, RF pulse phase, number of RF pulses, type of gradient applied between an excitation portion of a sequence block and a readout portion of a sequence block, number of gradients applied between an excitation portion of a sequence block and a readout portion of a sequence block, type of gradient applied between a readout portion of a sequence block and an excitation portion of a sequence block, number of gradients applied between a readout portion of a sequence block and an excitation portion of a sequence block, type of gradient applied during a readout portion of a sequence block, number of gradients applied during a readout portion of a sequence block, amount of RF spoiling, or amount of gradient spoiling. In different embodiments two, three, four, or more parameters may vary between sequence blocks. In different embodiments, the number of parameters varied between sequence blocks may itself vary. For example, A1 (sequence block 1) may differ from A2 in five parameters, A2 may differ from A3 in seven parameters, A3 may differ from A4 in two parameters, and so on. One skilled in the art will appreciate that there are a nearly infinite number of series of sequence blocks that can be created by varying this large number of parameters. Note also that while phase 340 may, in some examples, be a preparation phase or preparation-like phase, that phase 340 does not necessarily perform a conventional image-centric preparation.

Figure 5:
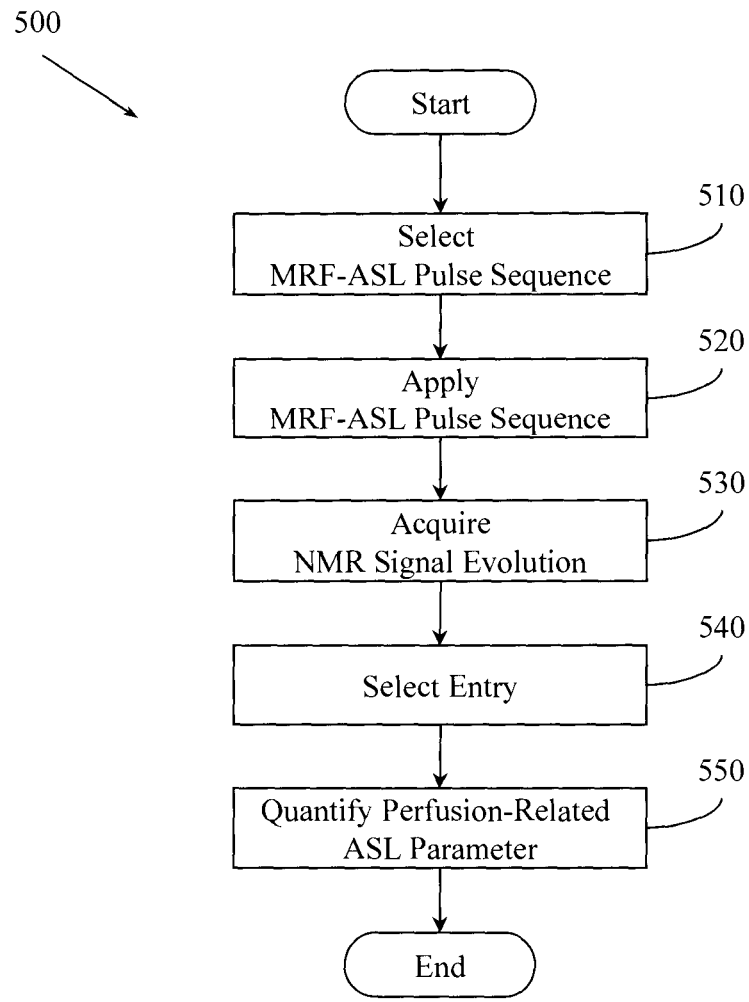
FIG. 5 illustrates an example method associated with ASL with MRF.

FIG. 5 illustrates a method 500 for performing ASL with MRF. Method 500 includes, at 510, selecting an ASL-MRF pulse sequence to apply to an object. Selecting an ASL-MRF pulse sequence may include identifying a pre-defined sequence that is available in a library. One or more attributes of the pre-defined sequence may be customized for a particular instance of method 500. Selecting an ASL-MRF pulse sequence may also include fabricating or defining a pulse sequence. Since the ASL-MRF pulse sequence will be used in ASL, in one embodiment, the ASL-MRF pulse sequence includes a labeling pulse and a control pulse.

Different ASL-MRF pulse sequences may be available for selection. In one embodiment, an ASL-MRF pulse sequence that has a pseudo-continuous ASL (PCASL) labeling scheme may be selected. In one embodiment, the PCASL labeling scheme may be described by a function $L(t)$, where $L(t)=1$ during a labeling pulse, $L(t)=-1$ during a control pulse, and $L(t)=0$ during post label delay and data acquisition. Due to the flexibility afforded by MRF, other functions may be employed.

In one embodiment, the ASL-MRF pulse sequence may include alternating labeling pulses and control pulses. While alternating labeling pulses and control pulses are described, labeling pulses and control pulses do not need to be presented one-for-one in lock-step fashion. For example, an ASL-MRF pulse sequence may present various numbers of varying labeling pulses and control pulses in varying orders (e.g., one labeling pulse, one control pulse, two labeling pulses, one control pulse, three labeling pulses, two control pulses, one labeling pulse, two control pulses, . . . ). In one embodiment, due to the flexibility of MRF, the ASL-MRF pulse sequence includes a non-uniform arrangement of non-uniform background suppression pulses, non-uniform acquisition periods, or non-uniform acquisition FA.

More generally, the ASL-MRF pulse sequence may include a non-uniform (e.g., random) arrangement of control pulses or label pulses. The control pulses and label pulses may have varying, non-uniform (e.g., random) attributes. For example, the control pulses may have varying duration or the label pulses may have varying tagging duration. Having varying, non-uniform, or random attributes and elements facilitates producing more unique signal evolution time courses than may be possible with conventional approaches, thereby improving over conventional approaches by producing a richer data set from which parameters can be quantified.

Method 500 also includes, at 520, controlling an MR apparatus to apply the ASL-MRF pulse sequence to the object. Applying the ASL-MRF pulse sequence may include controlling the MR apparatus to enter a transmit mode where gradients and RF pulses are controlled. Applying the ASL-MRF pulse sequence may cause arterial spins to be labelled. Because blood moves around in the body, after being labeled the arterial spins may be delivered to a portion of the object over time. In one embodiment, the arterial spins may be delivered according to a variable arterial input function. The ASL-MRF pulse sequence may produce non-uniform post-labeling decay in the NMR signal evolution acquired from the object. Once again, producing a greater number of more unique signal evolution time courses than conventional approaches may provide a richer data set from which parameters can be quantified.

Method 500 also includes, at 530, acquiring an NMR signal evolution from the object. Acquiring the NMR signal evolution may include controlling an MRI apparatus to enter a receive mode. The NMR signal evolution depends, at least in part, on the arterial spins. For example, the labeled arterial spins may change the magnetization of a tissue and that change may be detectable by MR apparatus.

Method 500 also includes, at 540, selecting an entry in an MRF dictionary associated with the NMR signal evolution. The entry may be selected using a pattern matching approach. For example, a best fit may be selected based on maximizing an inner product between an acquired signal evolution and a stored signal evolution.

Method 500 also includes, at 550, simultaneously quantifying two or more properties of the arterial spins for the object. The quantification may be based, at least in part, on the entry. For example, the entry selected from the MRF dictionary may have quantified values for the parameters associated with the entry. The properties may include, for example, CBF, transit time, or T1 relaxation.

Figure 6:
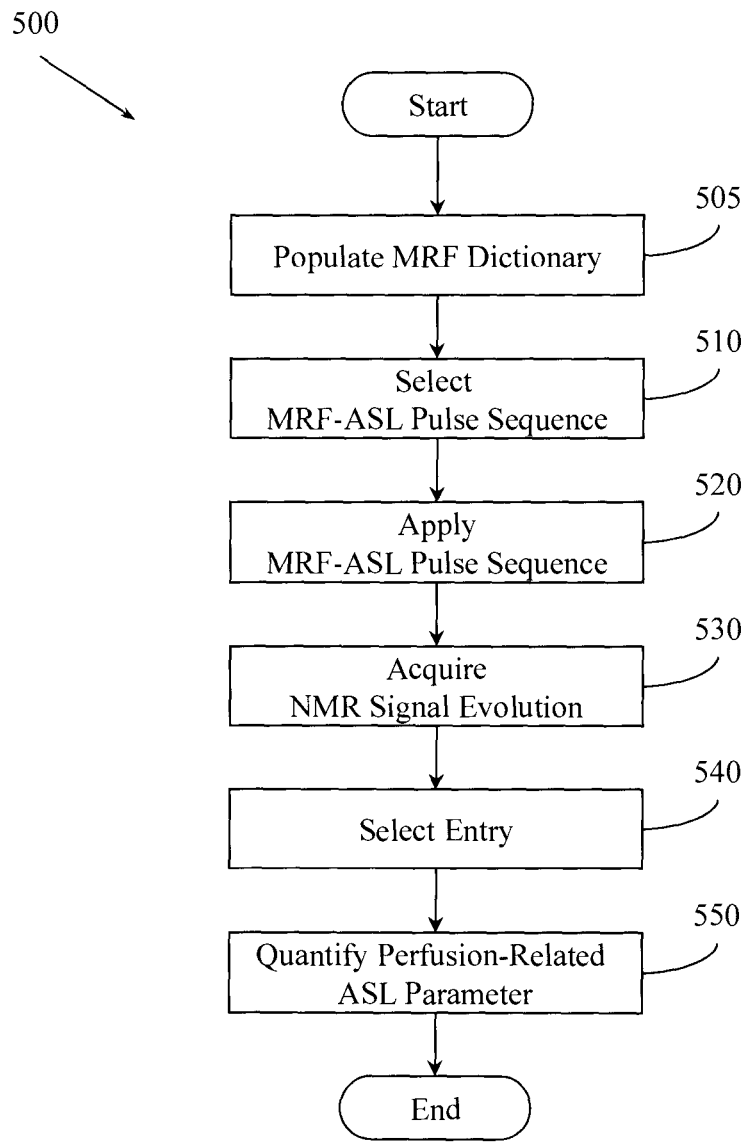
FIG. 6 illustrates an example method associated with ASL with MRF.

FIG. 6 illustrates another embodiment of method 500. This embodiment may include, at 505, populating the MRF dictionary with signal evolutions that are useful to or particular to ASL. For example, populating the MRF dictionary at 505 may include adding to the MRF dictionary signal evolutions that describe inflow and outflow of labeled spins according to equation 1. Populating the MRF dictionary at 505 may, additionally or alternatively, include adding to the MRF dictionary signal evolutions that model arterial input according to equations 2 or 3. Populating the MRF dictionary at 505 may include, additionally or alternatively, adding to the MRF dictionary signal evolutions described by:

$$SE = \sum_{s=1}^{N_S} \prod_{i=1}^{N_A} \sum_{j=1}^{N_{RF}} R_i(\alpha) R_{RF_{ij}}(\alpha, \phi) R(G) E_i(T1, T2, F) M_0 \quad [4]$$

or $$SE = \sum_{s=1}^{N_S} \prod_{i=1}^{N_A} \prod_{j=1}^{N_{RF}} R_i(\alpha) R_{RF_{ij}}(\alpha, \phi) R(G) E_i(T1, T2, F) M_0 \quad [5]$$

where:
SE is a signal evolution,
$N_S$ is a number of spins,
$N_A$ is a number of sequence blocks,
$N_{RF}$ is a number of RF pulses in a sequence block,
α is a flip angle,
φ is a phase angle,
Ri(α) is a rotation due to off resonance,
$R_{RF_{ij}}(\alpha, \phi)$ is a rotation due to RF differences,
R(G) is a rotation due to a gradient,
T1 is spin-lattice relaxation,
T2 is spin-spin relaxation,
F is the effects of the properties of the arterial spins,
$E_i(T1,T2,F)$ is decay due to relaxation differences, and
$M_0$ is the default or equilibrium magnetization.

Populating the MRF dictionary at 505 may include, additionally or alternatively, adding to the MRF dictionary signal evolutions described by:

$$S_i = R_i E_i (S_{i-1}) \quad [6]$$

or $$S_i = R_i E_i \sum_{x=1}^{i-1} R_x E_x (S_x) \quad [7]$$

or $$S_i = R_i E_i \prod_{x=1}^{i-1} R_x E_x (S_x) \quad [8]$$

where:
$S_0$ is the default or equilibrium magnetization,
$S_i$ is a vector that represents the different components of the magnetization Mx, My, Mz during acquisition block i,
$R_i$ is the combination of rotational effects that occur during acquisition block i, and
$E_i$ is the combination of effects that alter the amount of magnetization in the different states for acquisition block i.

Populating the MRF dictionary at 505 may include, additionally or alternatively, adding to the MRF dictionary signal evolutions described by:

$$S_i = \sum_{s=1}^{N_S} R_{s,i} E_{s,i} (S_{s,i-1}) \quad [9]$$

or $$S_i = \sum_{s=1}^{N_S} R_{s,i} E_{s,i} \sum_{x=1}^{i-1} R_{s,x} E_{s,x} (S_{s,x}) \quad [10]$$

or $$S_i = \sum_{s=1}^{N_S} R_{s,i} E_{s,i} \prod_{x=1}^{i-1} R_{s,x} E_{s,x} (S_{s,x}) \quad [11]$$

where:
$S_0$ is the default or equilibrium magnetization,
Ns is the number of spins,
$S_i$ is a vector that represents the different components of the magnetization Mx, My, Mz during acquisition block i,
$R_{i,s}$ is the sum of rotational effects that occur during acquisition block i for spin s, and
$E_{i,s}$ is the sum of effects that alter the amount of magnetization in the different states for acquisition block i for spin s.

Figure 7:
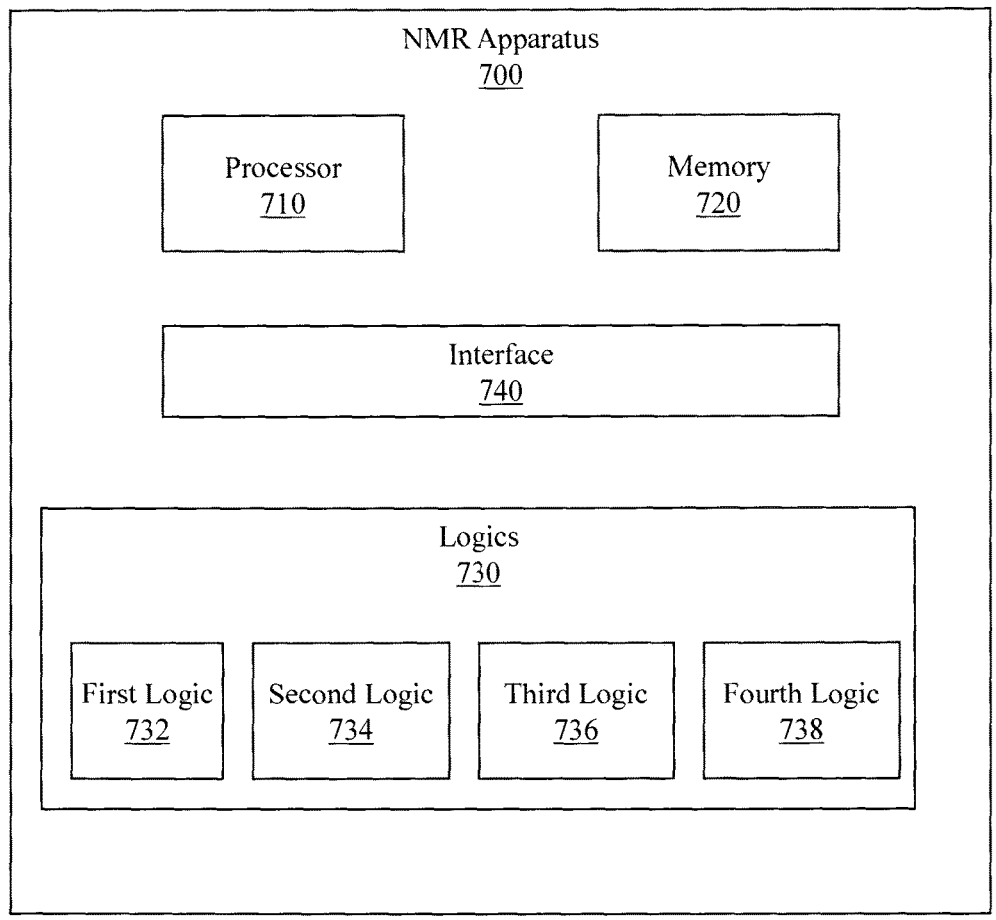
FIG. 7 illustrates an example apparatus associated with ASL with MRF.

FIG. 7 illustrates an NMR apparatus 700. NMR apparatus 700 includes a processor 710 and memory 720 that are connected to a set of logics 730 by an interface 740. NMR apparatus 700 includes a first logic 732 that prepares an ASL-MRF pulse sequence. Preparing an ASL-MRF pulse sequence may involve setting values for pulse sequence parameters. The pulse sequence parameters may include the type of pulses to be employed, the number of pulses to be employed, the order in which pulses will be employed, or other attributes of a pulse. In one embodiment, the first logic 732 prepares the ASL-MRF pulse sequence with varying labeling pulses and varying control pulses. Setting values for the pulse sequence parameters may include changing the value in a computer memory, changing a value in a register, or changing a value in some other computer hardware or circuit.

In one embodiment, the first logic 732 prepares the ASL-MRF pulse sequence with varying background suppression pulses, varying acquisition periods, or varying FA. Other attributes may be varied. In one embodiment, the labeling pulses conform to a PCASL labeling scheme. Other labeling schemes may be employed.

Apparatus 700 also includes a second logic 734 that causes arterial spins in an object to be selectively labeled by controlling the NMR apparatus to apply the ASL-MRF pulse sequence to the object. Apparatus 700 also includes a third logic 736 that acquires a signal evolution of an NMR signal produced by the labeled arterial spins and the object in response to the ASL-MRF pulse sequence.

Apparatus 700 also includes a fourth logic 738 that retrieves one or more perfusion-related ASL parameters for the object. The perfusion-related parameters may be retrieved from an MRF dictionary. The perfusion-related parameters that are retrieved may be selected using the signal evolution. The perfusion-related ASL parameters may include, for example, CBF, transit time, and T1 relaxation.

Figure 8:
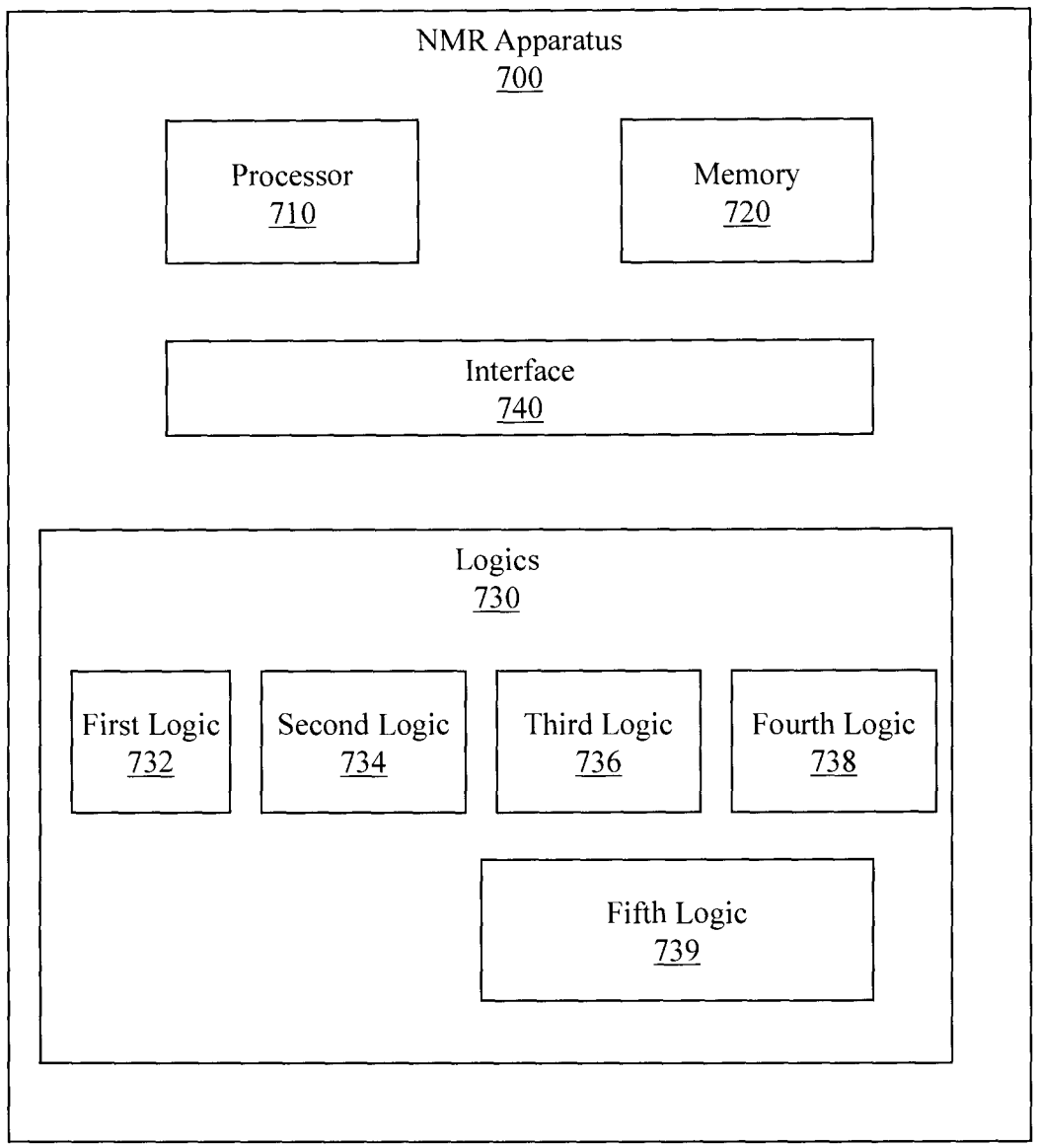
FIG. 8 illustrates an example apparatus associated with ASL with MRF.

FIG. 8 illustrates another embodiment of apparatus 700. This embodiment of apparatus 700 includes a fifth logic 739 that populates the MRF dictionary with signal evolutions that account for inflow or outflow of labeled spins according to equation 1. In one embodiment, the fifth logic 739 populates the MRF dictionary with signal evolutions that account for arterial input according to equations 2 or 3. The fifth logic 739 may also populate the MRF dictionary with signal evolutions described by equations 4-11.

Figure 9:
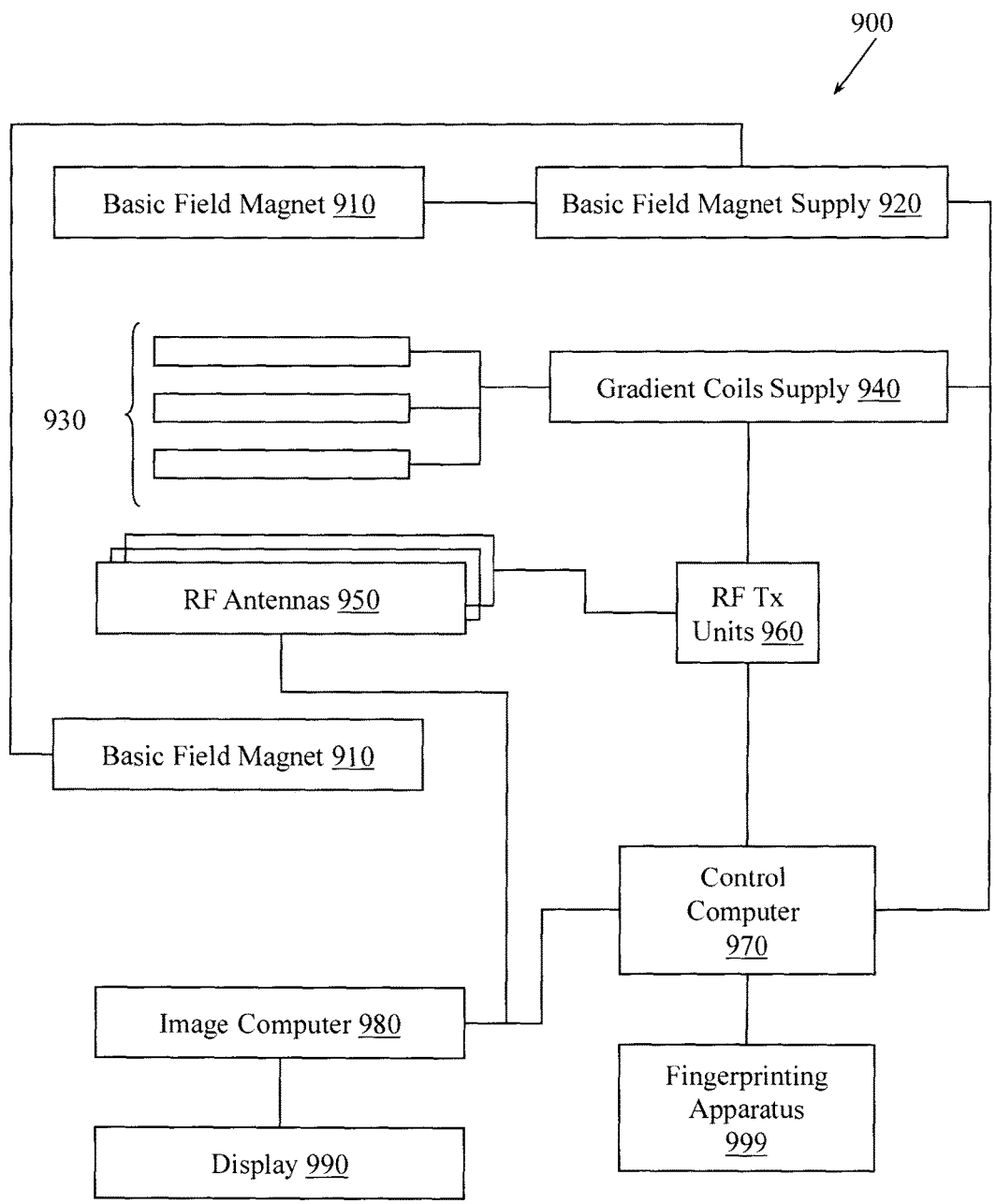
FIG. 9 illustrates an example MRI apparatus that performs ASL with MRF.

FIG. 9 illustrates an example MRI apparatus 900 that has a fingerprinting apparatus 999 to facilitate MRI fingerprinting. The fingerprinting apparatus 999 may have elements of example apparatus described herein and/or may perform example methods described herein. For example, the fingerprinting apparatus 999 may have circuits or logics that simultaneously quantify multiple ASL perfusion-related parameters.

In one embodiment, fingerprinting apparatus 999 may perform a method for quantifying an ASL perfusion-related parameter that includes labeling arterial spins using an MRF pulse sequence having unmatched label pulses and control pulses. In addition to the label pulses and control pulses not being presented lock-step in pairs, the control pulses may vary and the label pulses may vary. The varying pulses may have non-uniform attributes (e.g., duration, order). In one embodiment, the pulses may vary randomly.

The MRF pulse sequence will label arterial spins, which will in turn transit in a body and have a discernible effect on one or more portions of the body. Thus, the method may include acquiring an NMR signal time course that depends, at least in part, on the arterial spins. Once the NMR signal time course has been acquired, the method may include quantifying the ASL perfusion-related parameter. The ASL perfusion-related parameter may be quantified using information retrieved from an MRF dictionary. The information may be retrieved from the MRF dictionary as a function of the NMR signal time course. For example, the entry may be used as an index into a table or database where quantified values are stored.

The MRF pulse sequence may differ from conventional pulse sequences in one or more ways. For example, the MRF pulse sequence may include non-uniform post labeling delay time, non-uniform or even random background suppression pulses located at varying or even random intervals in the MRF pulse sequence, background suppression pulses with varying or even random durations, varying or even random acquisition repetition times, or varying or even random acquisition flip angles.

The apparatus 900 includes a basic field magnet(s) 910 and a basic field magnet supply 920. Ideally, the basic field magnets 910 would produce a uniform $B_0$ field. However, in practice, the $B_0$ field may not be uniform, and may vary over an object being imaged by the MRI apparatus 900. MRI apparatus 900 may include gradient coils 930 configured to emit gradient magnetic fields like $G_S$, $G_P$ and $G_R$. The gradient coils 930 may be controlled, at least in part, by a gradient coils supply 940. In some examples, the timing, strength, and orientation of the gradient magnetic fields may be controlled, and thus selectively adapted, during an MRI procedure.

MRI apparatus 900 may include a set of RF antennas 950 that generate RF pulses and receive resulting NMR signals from an object to which the RF pulses are directed. In some examples, how the pulses are generated and how the resulting MR signals are received may be controlled and thus may be selectively adapted during an MR procedure. Separate RF transmission and reception coils can be employed. The RF antennas 950 may be controlled, at least in part, by a set of RF transmission units 960. An RF transmission unit 960 may provide a signal to an RF antenna 950.

The gradient coils supply 940 and the RF transmission units 960 may be controlled, at least in part, by a control computer 970. In one example, the control computer 970 may be programmed to control an NMR device as described herein. Conventionally, the MR signals received from the RF antennas 950 can be employed to generate an image and thus may be subject to a transformation process like a two dimensional Fast Fourier Transform (FFT) that generates pixilated image data. The transformation can be performed by an image computer 980 or other similar processing device. The image data may then be shown on a display 990.

However, fingerprinting apparatus 999 facilitates not having to do conventional reconstruction of an image from MR signals received from the RF antennas 950. Thus the RF energy applied to an object by apparatus 900 need not be constrained to produce signals with substantially constant amplitudes or phases. Instead, fingerprinting apparatus 999 facilitates matching received signals to known signals for which a reconstruction, relaxation parameter, or other information is already available. This facilitates producing a quantitative result.

While FIG. 9 illustrates an example MRI apparatus 900 that includes various components connected in various ways, it is to be appreciated that other MRI apparatus may include other components connected in other ways.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Logic", as used herein, includes but is not limited to hardware, firmware, software in execution on a machine, or combinations of each to perform a function(s) or an action(s), or to cause a function or action from another logic, method, or system. Logic may include a software controlled microprocessor, a discrete logic (e.g., ASIC), an analog circuit, a digital circuit, a programmed logic device, a memory device containing instructions, and other physical devices. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

In one embodiment, the functionality associated with a logic may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs).

"User", as used herein, includes but is not limited to one or more persons, software, computers or other devices, or combinations of these.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

What is claimed is:

1. A method for performing arterial spin labeling (ASL) with magnetic resonance fingerprinting (MRF), comprising:
   selecting an ASL-MRF pulse sequence to apply to an object, where the ASL-MRF pulse sequence includes a labeling pulse and a control pulse;
   controlling a magnetic resonance (MR) apparatus to apply the ASL-MRF pulse sequence to the object;
   acquiring a nuclear magnetic resonance (NMR) signal evolution from the object, where the NMR signal evolution depends, at least in part, on a property of the arterial spins in the object;
   selecting an entry in an MRF dictionary associated with the NMR signal evolution, and
   simultaneously quantifying two or more properties of the arterial spins in the object based, at least in part, on the entry.

2. The method of claim 1, where the two or more properties of the arterial spins include cerebral blood flow (CBF), transit time, or T1 relaxation.

3. The method of claim 1, where the ASL-MRF pulse sequence has a pseudo-continuous ASL (PCASL) labeling scheme.

4. The method of claim 3, where the PCASL labeling scheme is described by a function L(t), where L(t) is positive during a labeling pulse, L(t) is negative during a control pulse, and L(t)=0 during post label delay and data acquisition.

5. The method of claim 3, where applying the ASL-MRF pulse sequence causes arterial spins to be delivered to a portion of the object over time according to a variable arterial input function.

6. The method of claim 1, where the ASL-MRF pulse sequence includes alternating labeling pulses and control pulses.

7. The method of claim 1, where the ASL-MRF pulse sequence includes a non-uniform arrangement of non-uniform background suppression pulses, non-uniform acquisition periods, or non-uniform acquisition flip angles (FA).

8. The method of claim 7, where the ASL-MRF pulse sequence produces non-uniform post-labeling decay in the NMR signal evolution acquired from the object.

9. The method of claim 1, where the ASL-MRF pulse sequence includes a non-uniform arrangement of control pulses and label pulses.

10. The method of claim 9, where the ASL-MRF pulse sequence includes control pulses with varying duration or label pulses with varying tagging duration.

11. The method of claim 1, comprising populating the MRF dictionary with signal evolutions that describe inflow or outflow of labeled spins according to:

$$\frac{dM}{dt} = \frac{M_0 - M}{T_1} + fM_a(t) - \frac{f}{\lambda}M$$

where M is the magnetization in brain tissue,
$M_0$ is the default or equilibrium magnetization,
$T_1$ is the T1 value for tissue,
$M_a(t)$ is the magnetization of labeled arterial blood,
f is perfusion,
$\lambda$ is a blood volume fraction associated with how much of a voxel is filled with blood,
$\Delta t$ is the transit time of blood,
$k(t-\Delta t)$ is a function to capture arterial dispersion, and
L(t) is the labeling function that indicates the occurrence of inversion pulses.

12. The method of claim 11, comprising populating the MRF dictionary with signal evolutions that model arterial input according to:

$$M_a(t) = M_0(1-2\alpha e^{-\Delta t/T_{1,a}})*k(t-\Delta t), \text{ if } L(t)=1$$

$$M_a(t) = M_0(1-e^{-\Delta t/T_{1,a}})*k(t-\Delta t), \text{ if } L(t) \neq 1$$

where M is the magnetization in brain tissue,
$M_0$ is the default or equilibrium magnetization,
$T_1$ and $T_{1,a}$ are the $T_1$ values for tissue and blood,
$M_a(t)$ is the magnetization of labeled arterial blood,
f is perfusion,
$\alpha$ is an inversion imperfection factor,
$\Delta t$ is the transit time of blood,
$k(t-\Delta t)$ is a function to capture arterial dispersion, and
L(t) is the labeling function that indicates the occurrence of inversion pulses.

13. The method of claim 1, comprising populating the MRF dictionary with signal evolutions described by:

$$SE = \sum_{s=1}^{N_S} \prod_{i=1}^{N_A} \sum_{j=1}^{N_{RF}} R_i(\alpha) R_{RF_{ij}}(\alpha, \phi) R(G) E_i(T1, T2, F) M_0$$

or $$SE = \sum_{s=1}^{N_S} \prod_{i=1}^{N_A} \prod_{j=1}^{N_{RF}} R_i(\alpha) R_{RF_{ij}}(\alpha, \phi) R(G) E_i(T1, T2, F) M_0$$

where:
SE is a signal evolution,
$N_S$ is a number of spins,
$N_A$ is a number of sequence blocks,
$N_{RF}$ is a number of RF pulses in a sequence block,
$\alpha$ is a flip angle,
$\phi$ is a phase angle, $R_i(\alpha)$ is a rotation due to off resonance,
$R_{RFij}(\alpha,\phi)$ is a rotation due to RF differences,
$R(G)$ is a rotation due to a gradient,
T1 is spin-lattice relaxation,
T2 is spin-spin relaxation,
F is the effects of the properties of the arterial spins,
$E_i(T1,T2,F)$ is decay due to relaxation differences, and
$M_0$ is the default or equilibrium magnetization.

14. The method of claim 1, comprising populating the MRF dictionary with signal evolutions described by:

$$S_i = R_i E_i(S_{i-1})$$

or $$S_i = R_i E_i \sum_{x=1}^{i-1} R_x E_x(S_x)$$

or $$S_i = R_i E_i \prod_{x=1}^{i-1} R_x E_x(S_x)$$

where:
$S_0$ is the default or equilibrium magnetization,
$S_i$ is a vector that represents the different components of the magnetization Mx, My, Mz during acquisition block i,
$R_i$ is the combination of rotational effects that occur during acquisition block i, and
$E_i$ is the combination of effects that alter the amount of magnetization in the different states for acquisition block i.

15. The method of claim 1, comprising populating the MRF dictionary with signal evolutions described by:

$$S_i = \sum_{s=1}^{N_s} R_{s,i} E_{s,i}(S_{s,i-1})$$

or $$S_i = \sum_{s=1}^{N_s} R_{s,i} E_{s,i} \sum_{x=1}^{i-1} R_{s,x} E_{s,x}(S_{s,x})$$

or $$S_i = \sum_{s=1}^{N_s} R_{s,i} E_{s,i} \prod_{x=1}^{i-1} R_{s,x} E_{s,x}(S_{s,x})$$

where:
$S_0$ is the default or equilibrium magnetization,
Ns is the number of spins,
$S_i$ is a vector that represents the different components of the magnetization Mx, My, Mz during acquisition block i,
$R_{i,s}$ is the sum of rotational effects that occur during acquisition block i for spin s, and
$E_{i,s}$ is the sum of effects that alter the amount of magnetization in the different states for acquisition block i for spin s.

16. A nuclear magnetic resonance (NMR) apparatus, comprising:
a first logic that prepares an arterial spin labeling (ASL) magnetic resonance fingerprinting (MRF) pulse sequence;
a second logic that causes arterial spins in an object to be selectively labeled by controlling the NMR apparatus to apply the ASL-MRF pulse sequence to the object;
a third logic that acquires a signal evolution of a nuclear magnetic resonance (NMR) signal produced by the labeled arterial spins and the object in response to the ASL-MRF pulse sequence, and
a fourth logic that retrieves, as a function of the signal evolution, from an MRF dictionary, one or more perfusion-related ASL parameters for the object.

17. The NMR apparatus of claim 16, where the one or more perfusion-related ASL parameters include cerebral blood flow (CBF), transit time, and T1 relaxation.

18. The NMR apparatus of claim 16, where the first logic prepares the ASL-MRF pulse sequence with varying labeling pulses and varying control pulses.

19. The NMR apparatus of claim 18, where the labeling pulses conform to a pseudo-continuous ASL (PCASL) labeling scheme.

20. The NMR apparatus of claim 18, where the first logic prepares the ASL-MRF pulse sequence with varying background suppression pulses, varying acquisition periods, or varying flip angles (FA).

21. The NMR apparatus of claim 18, comprising a fifth logic that populates the MRF dictionary with signal evolutions that account for inflow or outflow of labeled spins according to:

$$\frac{dM}{dt} = \frac{M_0 - M}{T_1} + fM_a(t) - \frac{f}{\lambda}M$$

where M is the magnetization in brain tissue,
$M_0$ is the default or equilibrium tissue magnetization,
$T_1$ is the T1 value for tissue,
$M_a(t)$ is the magnetization of labeled arterial blood,
f is perfusion,
$\lambda$ is a blood volume fraction associated with how much of a voxel is filled with blood,
$\Delta t$ is the transit time of blood,
$k(t-\Delta t)$ is a function to capture arterial dispersion, and
L(t) is the labeling function that indicates the occurrence of inversion pulses.

22. The NMR apparatus of claim 21, where the fifth logic populates the MRF dictionary with signal evolutions that account for arterial input according to:

$$M_a(t) = M_0(1 - 2\alpha e^{-\Delta t/T_{1,a}}) * k(t-\Delta t), \text{ if } L(t)=1$$

$$M_a(t) = M_0(1 - e^{-\Delta t/T_{1,a}}) * k(t-\Delta t), \text{ if } L(t) \neq 1$$

where M is the magnetization in brain tissue,
$M_0$ is the default or equilibrium tissue magnetization,
$T_1$ and $T_{1,a}$ are the $T_1$ values for tissue and blood,
$M_a(t)$ is the magnetization of labeled arterial blood,
f is perfusion,
$\alpha$ is an inversion imperfection factor,
$\Delta t$ is the transit time of blood,
$k(t-\Delta t)$ is a function to capture arterial dispersion, and
L(t) is the labeling function that indicates the occurrence of inversion pulses.

23. The NMR apparatus of claim 16, where the fifth logic populates the MRF dictionary with signal evolutions described by:

$$SE = \sum_{s=1}^{N_s} \prod_{i=1}^{N_A} \sum_{j=1}^{N_{RF}} R_i(\alpha) R_{RFij}(\alpha, \phi) R(G) E_i(T1, T2, F) M_0$$

or

-continued $$SE = \sum_{s=1}^{N_s} \prod_{i=1}^{N_A} \prod_{j=1}^{N_{RF}} R_i(\alpha) R_{RF_{ij}}(\alpha, \phi) R(G) E_i(T1, T2, F) M_0$$

where:
SE is a signal evolution,
$N_S$ is a number of spins,
$N_A$ is a number of sequence blocks,
$N_{RF}$ is a number of RF pulses in a sequence block,
α is a flip angle,
φ is a phase angle,
Ri(a) is a rotation due to off resonance,
$R_{RFij}(\alpha,\phi)$ is a rotation due to RF differences,
R(G) is a rotation due to a gradient,
T1 is spin-lattice relaxation,
T2 is spin-spin relaxation,
F is the effects of the properties of the arterial spins,
$E_i(T1,T2,F)$ is decay due to relaxation differences, and
$M_0$ is the default or equilibrium magnetization.

24. The NMR apparatus of claim 16, where the fifth logic populates the MRF dictionary with signal evolutions described by:

$$S_i = R_i E_i(S_{i-1})$$

or $$S_i = R_i E_i \sum_{x=1}^{i-1} R_x E_x(S_x)$$

or $$S_i = R_i E_i \prod_{x=1}^{i-1} R_x E_x(S_x)$$

where:
$S_0$ is the default or equilibrium magnetization.
$S_i$ is a vector that represents the different components of the magnetization Mx, My, Mz during acquisition block i,
$R_i$ is the combination of rotational effects that occur during acquisition block i, and
$E_i$ is the combination of effects that alter the amount of magnetization in the different states for acquisition block i.

25. The NMR apparatus of claim 16, where the fifth logic populates the MRF dictionary with signal evolutions described by:

$$S_i = \sum_{s=1}^{N_s} R_{s,i} E_{s,i}(S_{s,i-1})$$

or $$S_i = \sum_{s=1}^{N_s} R_{s,i} E_{s,i} \sum_{x=1}^{i-1} R_{s,x} E_{s,x}(S_{s,x})$$

or $$S_i = \sum_{s=1}^{N_s} R_{s,i} E_{s,i} \prod_{x=1}^{i-1} R_{s,x} E_{s,x}(S_{s,x})$$

where:
$S_0$ is the default or equilibrium magnetization,
Ns is the number of spins,
$S_i$ is a vector that represents the different components of the magnetization Mx, My, Mz during acquisition block i,
$R_{i,s}$ is the sum of rotational effects that occur during acquisition block i for spin s, and
$E_{i,s}$ is the sum of effects that alter the amount of magnetization in the different states for acquisition block i for spin s.

26. A method for quantifying an arterial spin labeling (ASL) perfusion-related parameter, comprising:
labeling arterial spins using a magnetic resonance fingerprinting (MRF) pulse sequence, where the MRF pulse sequence has non-uniform control pulses or non-uniform label pulses;
acquiring an NMR signal time course that depends, at least in part, on the arterial spins, and
quantifying the ASL perfusion-related parameter using information retrieved from an MRF dictionary as a function of the NMR signal time course.

27. The method of claim 26, where the MRF pulse sequence includes non-uniform post labeling delay time, background suppression pulses located at varying intervals in the MRF pulse sequence, background suppression pulses with varying durations, varying acquisition repetition times, or varying acquisition flip angles.

* * * * *